US005507787A

United States Patent [19]
Borghi

[11] Patent Number: 5,507,787
[45] Date of Patent: Apr. 16, 1996

[54] ADAPTOR DEVICE FOR ELECTRODE CATHETERS

[75] Inventor: Enzo Borghi, Budrio, Italy

[73] Assignee: X-Trode, S.r.l., Bologna, Italy

[21] Appl. No.: 401,877

[22] Filed: Mar. 10, 1995

[30] Foreign Application Priority Data

Mar. 15, 1994 [IT] Italy ................. BO94A0102

[51] Int. Cl.$^6$ ................................................ A61N 1/05
[52] U.S. Cl. ................................................ 607/37; 439/909
[58] Field of Search .................. 607/37, 119, 2; 128/642, 772; 439/909

[56] References Cited

U.S. PATENT DOCUMENTS

| 4,112,953 | 9/1978 | Shanker et al. | 607/37 |
|---|---|---|---|
| 5,174,289 | 12/1992 | Cohen. | |
| 5,207,683 | 5/1993 | Goode et al. | 606/1 |
| 5,324,312 | 6/1994 | Stokes et al. | 607/37 |
| 5,336,251 | 8/1994 | Borghi. | |

FOREIGN PATENT DOCUMENTS

| 506620 | 9/1992 | European Pat. Off.. |
|---|---|---|
| 574358 | 12/1993 | European Pat. Off.. |
| 3304506 | 8/1984 | Germany. |

Primary Examiner—William E. Kamm
Assistant Examiner—Kennedy J. Schaetzle
Attorney, Agent, or Firm—Fay, Sharpe, Beall, Fagan, Minnich & McKee

[57] ABSTRACT

The components of an adaptor device for use with cardiac pacemaker electrode catheters include a conductive element, typically a stilet, serving to ensure a sound connection between the already implanted spiral wound wire and a new pacemaker: in the improved adaptor, the conductive element is flexible, appearing as a further spiral wound wire secured by one end to a spindle and extending from the tip of the spindle along the entire length of the implanted wire in such a way as to terminate near the stimulation electrode, which is anchored in a ventricular wall of the cardiac muscle.

3 Claims, 3 Drawing Sheets

ADAPTOR DEVICE FOR ELECTRODE CATHETERS

BACKGROUND OF THE INVENTION

The present invention concerns an improvement to an adaptor device for implanted electrode catheters, in particular for unipolar electrode catheters. The art field of heart surgery embraces numerous types of cardiac catheter designed for connection at one end, generally by way of a flexible tube functioning as a biocompatible outer sheath, to an artificial pacemaker implanted in the body of the patient, and carrying a terminal electrode at the remaining end which is offered in direct contact (positively anchored in most instances), to the ventricular cardiac muscle.

In the particular case in point, the expression 'unipolar' is used to describe a catheter of which the terminal electrode constitutes the negative pole or cathode of the cardiac pacemaker, and the positive pole or anode is provided by the casing of the pacemaker itself.

The terminal or ventricular electrode consists in a sharp point, preferably affording elements such as will penetrate and thus establish a continuous and secure contact with the cardiac muscle, which is connected to the negative pole of the pacemaker by way of an electrically conductive spiral wound wire (e.g. platinum-iridium alloy).

It is being found currently, where patients require the replacement of an existing pacemaker rendered unreliable by reason of its low charge, irregular operation or malfunction, that problems can arise due to incompatibilities between the connectors of electrode catheters implanted in the past and those of more recent design; reflecting the ever greater technological advances being made in this field, in effect, the newer catheters are much smaller than their predecessors as the overall dimensions of the newer pacemakers also become much smaller.

Remembering that the ventricular electrode becomes embedded in time beneath a layer of organic tissue and cannot be removed (such a step is inadvisable from the medical standpoint), it happens that the solution adopted in present-day surgical practice is almost invariably one of implanting a completely new electrode catheter in the cardiac cavity for connection to the new pacemaker, and simply leaving the former electrode in place, unused, alongside the replacement. The option also exists, however, of reutilizing the already implanted electrode by fitting a mechanical adaptor device.

Whatever the replacement method ultimately adopted, the fact that the patient has become reliant on the pacemaker dictates that artificial stimulation must be maintained for as long as is feasible: thus, any replacement operation, and especially the fitment of a mechanical adaptor, must be accomplished as swiftly as possible.

To this end, the applicant has already invented and produced an adaptor device for electrode catheters of the type in question (see U.S. Pat. No. 5,336,251), appearing as a combination of elements interposed between the spiral wound wire associated with an already implanted electrode and a pacemaker of the latest generation, by means of which the requisite mechanical and electrical connections between these two components can be made swiftly, without causing the patient discomfort, with high levels of safety and reliability, and utilizing shapes and volumes matched ergonomically to the requirements imposed by the smaller dimensions of the newer pacemakers. While on the one hand the problem of replacing a pacemaker in rapid time has been overcome with the patent adaptor, it has also emerged from tests on the device, carried out in conjunction with medical research into such problems, that the part of the implant which becomes the most delicate and exposed to the greatest risk is the spiral wound conductor already anchored to the cardiac muscle: in effect, the spiral structure can become strained locally over time, at intermediate points along its length, due mainly to the arched position occupied by the wire internally of the heart, and to the stresses the rhythmic movement of the heart can generate. This localized strain (whether partial or total) can obviously affect the passage of the electrical signal along the wire in either direction between electrode and pacemaker, causing inconsistencies that are hazardous for the patient.

Accordingly, the applicant has concluded that this serious drawback can be overcome by exploiting the existing solution of the adaptor device, and more exactly by improving the device itself: utilizing a basic structure similar to that of its predecessor, the improved device can be applied directly even to an already implanted electrode catheter, in such a way as to reinforce the catheter mechanically and ensure uninterrupted continuity of the electrical signal, even in the event of the spiral wound wire developing defects or undergoing strain.

SUMMARY OF THE INVENTION

The improvement according to the present invention is applicable to an adaptor device for unipolar cardiac pacemaker electrode catheters of the type comprising a first electrically conductive spiral wound wire connected at one end to the negative pole of a pacemaker (of which the casing provides the positive pole), inserted through an insulating flexible tubular sheath and fitted at the remaining end with a stimulation electrode anchored to the ventricular wall of a cardiac muscle.

The adaptor device is used in conjunction with an electrode catheter of which the original connector has been removed and the end of the first spiral wound wire exposed from the sheath, and comprises an electrically conductive rigid spindle rotatable about its own axis and occupying at least one end of an electrically conductive sleeve, a conductive element associated coaxially with one end of the spindle, which passes through and beyond the open end of the sleeve and is insertable coaxially through the first spiral wound wire, and a second electrically conductive spiral wound wire located internally of the sleeve, anchored thereto at one end, and interposed thus between the sleeve and the conductive element; the adaptor further comprises detachable means of rotation associated with the exposed end of the spindle and used by the surgeon to torque the second spiral wound wire so that its diameter is reduced, thereby restraining the first spiral wound wire against the conductive element, also fastening means applied externally to an outer second sheath and serving to pinch the first and second spiral wound wires together.

The improvement consists essentially in adopting a flexible conductive element, which takes the form of a third spiral wound wire secured by one end to the spindle and extending from the spindle along the entire length of the first spiral wound wire, so as to terminate near the stimulation electrode anchored in the cardiac muscle.

BRIEF DESCRIPTION OF THE DRAWINGS

The invention will now be described in detail, by way of example, with the aid of the accompanying drawings, in which.

DESCRIPTION OF THE PREFERRED EMBODIMENTS

Figure 1:
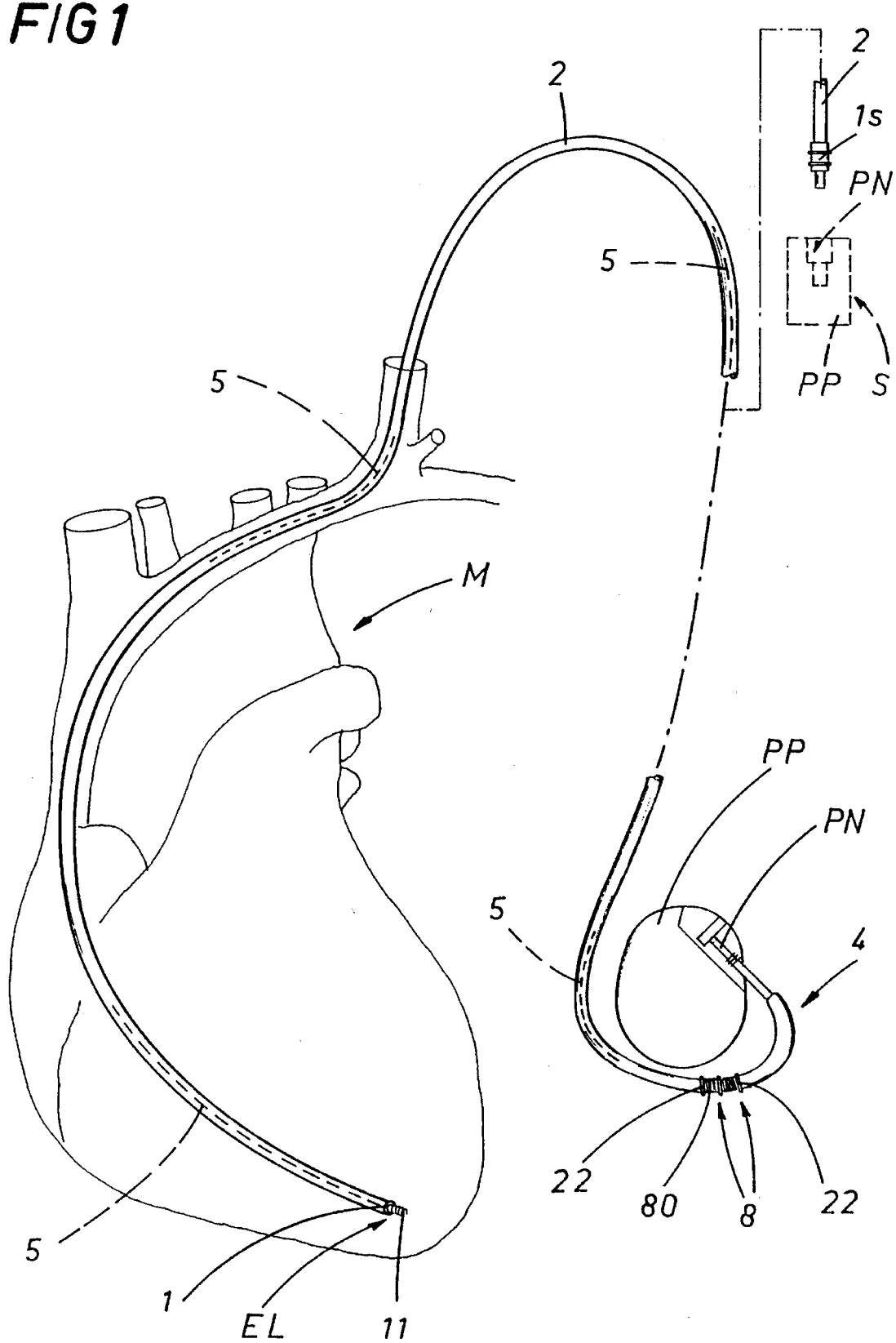
FIG. 1 is a sketch showing a typical unipolar electrode catheter as implanted conventionally in cardiac muscle, together with the improved adaptor according to the invention.

As illustrated in the drawings, the improvement to which the present invention relates is applied to an adaptor device designed for use in conjunction with cardiac pacemaker electrode catheters of unipolar type, that is, comprising an electrically conductive inner spiral wound wire 1 (see FIG. 1 in particular) connected at one end by a pin Is to the negative pole PN of a cardiac pacemaker denoted S (illustrated in phantom line), of which the casing provides the positive pole PP of the implant. This inner or first spiral wound wire 1 is ensheathed within a flexible tube 2 of electrically insulating material and associated at the end remote from the pin 1s with a conductive element 11 providing the stimulation electrode EL; the electrode engages in direct contact with the cardiac muscle M and, where appropriate, can be fashioned in such a manner (for example with a screw tip) as to anchor positively in the wall of the ventricle.

Figure 3:
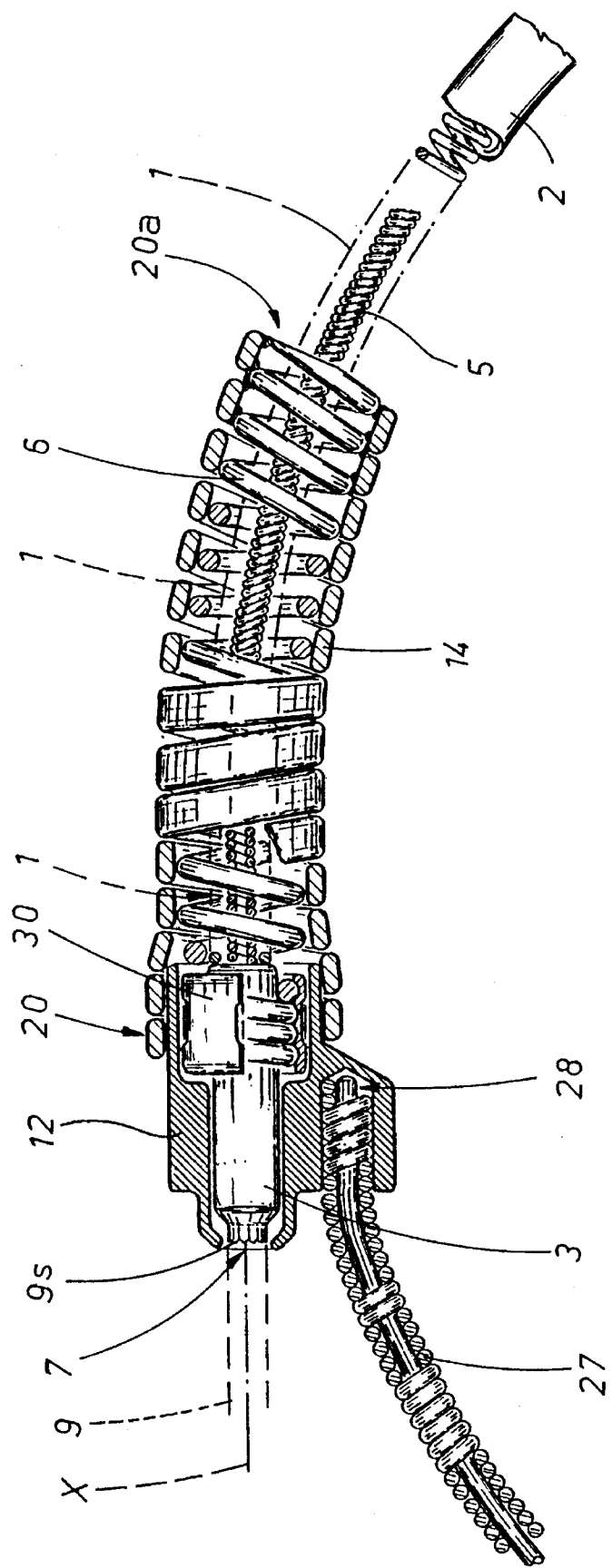
FIG. 3 is an enlarged detail of FIG. 2 which more clearly illustrates the improvement disclosed, viewed in a side elevation, partly in section and with certain parts cut away.

The adaptor device is used in conjunction with an existing electrode catheter of which the original electrode pin 1s aforementioned has been removed, and the sheath 2 cut back a suitable distance to expose the end ES of the first spiral wound wire 1 (as discernible clearly in FIG. 3).

An adaptor device of the type in question comprises (see FIG. 2): a sleeve 20, a spindle 3, a conductive element 5, a second sheath 4, a second spiral wound wire 6, rotation means 7 and fastening means 8. The spindle 3 is rigid and electrically conductive, insertable coaxially through the sleeve 20 to an exact fit, and rotatable thus about its own axis X; the sleeve 20 itself is fashioned in two distinct parts, as described more fully in due course, and affords a portion of lesser diameter constituting a terminal contact element denoted P (in practice, a new pin of diameter smaller than that of the pin 1s removed from the existing catheter and thus readily adaptable to the new dimensions of the replacement pacemaker).

At a given point internally of the sleeve 20, the spindle 3 is connected directly and coaxially with the conductive element 5, which projects from the open end 20a of the sleeve 20 and will exhibit an external diameter matched to the internal diameter of the first spiral wound wire 1, such that the one is insertable coaxially into the other.

The second spiral wound wire 6, also electrically conductive (manufactured, for example, and indeed preferably, from annealed platinum-iridium alloy), is accommodated internally of the sleeve 20 and anchored or soldered at the opposite ends to the open end 20a of the sleeve itself and to the end of the spindle 3 occupying the sleeve 20 (see FIG. 2), respectively; the internal diameter of the second spiral wound wire 6 is substantially identical to the external diameter of the electrode catheter 1, in such a manner that the one can be inserted coaxially into the other.

Figure 2:
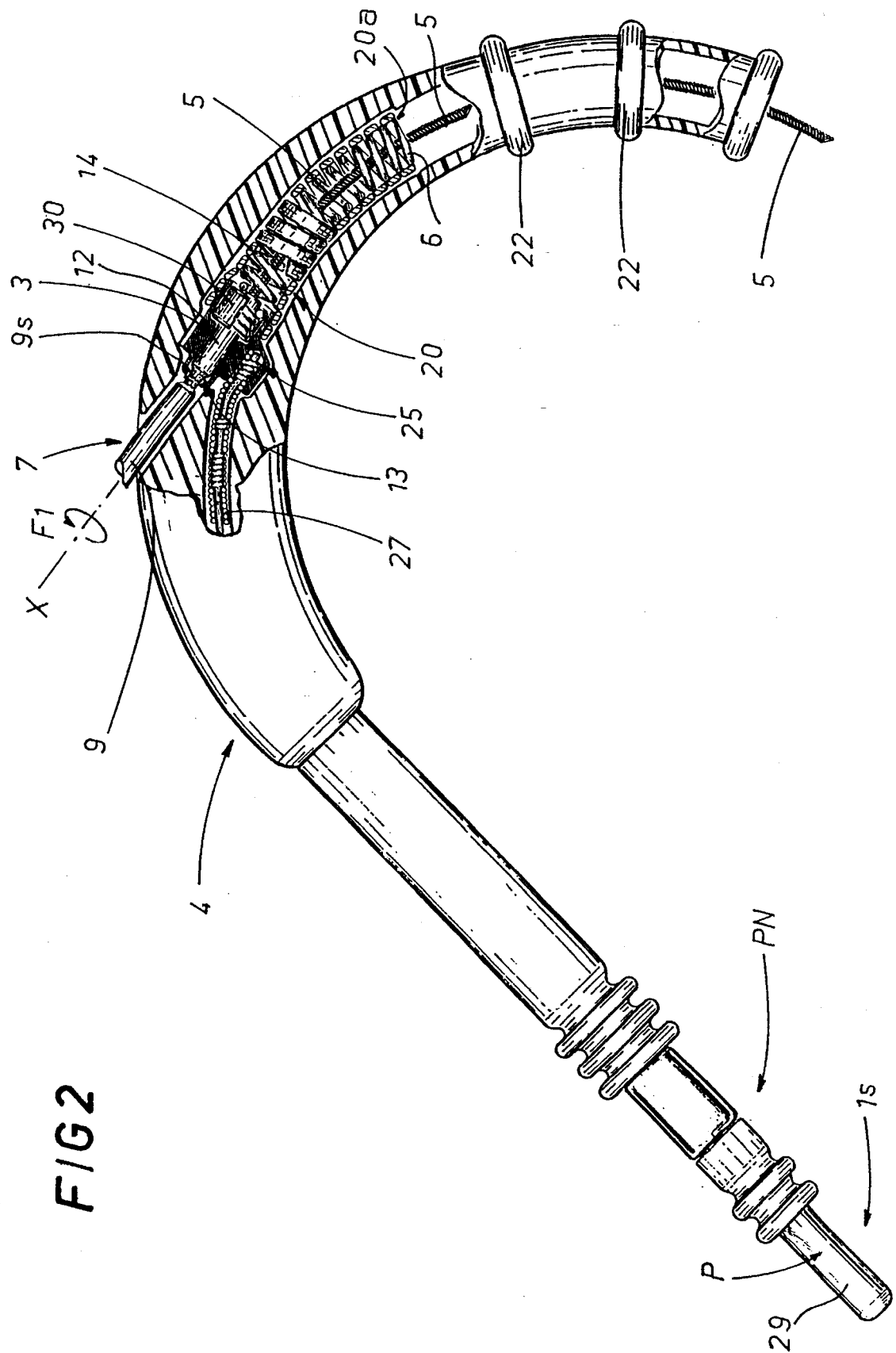
FIG. 2 illustrates the improvement according to the invention, applied to an adaptor connecting a spiral wound conductor and a cardiac pacemaker, in an enlarged side elevation viewed partly in section and with certain parts cut away.

The rotation means 7 (which are of detachable type) impinge on the free end of the spindle 3 emerging from the second sheath 4, and consist in a key 9 rigidly associated with the spindle 3 and affording a terminal portion fashioned as a handle that can be gripped and turned to rotate the spindle. The key 9 (which is illustrated only in part, being of conventional embodiment) will be seen to comprise a slender portion 9s, coinciding with the point of its association with the spindle 3 and serving to define a location at which fracture or separation occurs once a given value of torque is generated in rotation. In practice, the effect of rotating the key, hence also the spindle 3 and the second spiral wound wire 6 attached to the spindle, is to produce a torsion by which the diameter of the spiral is reduced, resulting ultimately in a stable retention of the first spiral wound wire 1 between the second wire 6 and the conductive element 5. FIGS. 2 and 3 of the drawings show an "ergonomic" solution made possible by virtue of the improvement disclosed, in which the conductive element 5 is of flexible embodiment and identifiable for practical purposes as a third electrically conductive spiral wound wire rigidly associated with the spindle 3; moreover, the length of the conductive element 5 is such that it will extend the full distance from the spindle to the element 11 anchored in the cardiac muscle M once the adaptor device is installed and operational.

The sleeve 20, as already intimated, is embodied in two distinct parts (likewise clearly discernible in FIGS. 2 and 3): the first such part 12 is rigid and affords a longitudinally disposed through socket 13 rotatably accommodating the spindle 3 and part of the key 9, while the second part 14 is flexible and tubular, secured on the one hand to one end of the first part 12 and extending on the other for the full length of the second spiral wound wire 6, to which it is likewise secured. In the particular example illustrated, this second part 14 of the sleeve 20 appears as a fourth spiral wound wire secured at a point coinciding with the end of the first part 12 affording the longitudinal socket 13, the socket being enlarged to receive the end of the second spiral wound wire 6, which is slipped over the spindle 3 and crimped in place by means of an electrically conductive collar 30.

As already established and extensively illustrated in the earlier solution (see U.S. Pat. No. 5,336,251), the rigid first part 12 of the sleeve incorporates a lateral branch 25 (consisting in a fifth spiral wound wire 27 accommodated internally of a relative socket 28 afforded by the first part 12) connected electrically to the main body of the sleeve 20 and extended, in this case coaxially with the remaining length of the second sheath 4 by which the sleeve is encapsulated, in such a manner that its free end (illustrated as a pin 29, one and the same as the pin 1s connected to the pacemaker S) provides the negative pole PN of the electrode catheter. The fastening means 8 consist in external binding elements 10 such as synthetic and/or biocompatible surgical thread applied to a predetermined area of the second sheath 4, compassed between a pair of suitably spaced rings 22, in such a way that the electrode catheter can be pinched internally of the adaptor and retained in a stable position.

The improved device thus described and illustrated is utilized in the following manner.

Having cut off and removed the existing connection pin 1s from the catheter originally implanted in the patient, the first sheath 2 is pared back from the cut end to expose a given length of the first spiral wound wire 1 (preferably a minimum 10 mm). At this juncture, having verified the length of the implanted electrode catheter and matched the length of the third spiral wound wire 5 accordingly, this same third spiral wound wire is inserted coaxially into the first spiral wound wire 1 by the surgeon and fed through until the tip locates the terminal part located internally of the cardiac muscle M, entering into contact preferably with the anchor element 11, and as full insertion is reached, the cut end of the first spiral wound wire 1 will also be ensheathed by the second spiral wound wire 6; thereupon, the key 9 is turned (arrow F1, FIG. 2), and the torsional force induced by rotation causes a reduction in diameter of the second spiral wound wire 6 which, being annealed, is unable to regain its former shape elastically, with the result that the first wire 1 remains locked stably against the third wire 5 internally of the second sheath 4 (see FIG. 3, phantom lines).

The operation in question is swiftly accomplished, and followed immediately by the step of binding the assembly at the area between the rings 22, thereby pinching the outer second sheath 4 securely against the inner first sheath 2 and ensuring a fluid-tight seal to prevent any infiltration.

This done, the rotation means 7 are either turned further or bent until a break occurs at the slender portion 9s connecting the key 9 and the spindle 3, whereupon the adaptor is ready for use and can be coupled without delay to the new pacemaker.

In addition to the acknowledged advantages of speed in effecting the changeover from an old to a new pacemaker, the improved solution disclosed brings a notable safety in operation generally, in the sense that the mechanical and electrical integrity of the first spiral wound wire can be restored. A further advantage is the division of the sleeve into two distinct parts, a feature that widens the scope for designing a device ergonomically tailored to the needs of the patient.

Moreover, it will be observed that with the two parts 12 and 14 of the sleeve 20 encapsulated in the manner illustrated, the surgeon is able to rely on a completely rigid connection between the three spiral wound wires 1, 5 and 6 during the operation of turning the key 9, thanks both to the action of the conductive collar 30 and to the embodiment of the socket 13 afforded by the rigid first part 12; in effect, the sleeve assembly affords a perfectly fluid-tight and mechanically secure anchorage to which the spiral wound conductors can be attached coaxially in suitably rigid and correct electrical association while retaining extreme flexibility along their entire length.

What is claimed:

1. In an adaptor device for unipolar cardiac pacemaker electrode catheters comprising a first electrically conductive spiral wound wire connected at one end by way of a pin to a negative pole of a cardiac pacemaker, of which a casing provides a positive pole of an implant, an insulating flexible tubular sheath accommodating the first spiral wound wire, and a stimulation electrode fitted to the remaining end of the first spiral wound wire and is adapted to be anchored to a ventricular wall of a cardiac muscle, applicable to an adaptor device designed for use in conjunction with an electrode catheter of which an original pin has been removed and the end of the first spiral wound wire being exposed from the sheath, and comprising, at least: an electrically conductive rigid spindle rotatable about its own axis and accommodated by at least one end of an electrically conductive sleeve; a conductive element associated coaxially with one end of the spindle, passing through and beyond the open end of the sleeve and insertable coaxially through the first spiral wound wire; a second electrically conductive spiral wound wire located internally of the sleeve, anchored at least to one end thereof and interposed thus between the sleeve and the conductive element; detachable means of rotation associated with the end of the spindle remote from the sleeve and impinging on the end of the second spiral wound wire for inducing a torsional stress resulting in the first spiral wound wire being restrained between the second spiral wound wire and the conductive element; also fastening means applied externally to an outer second sheath for securing the first and second spiral wound wires permanently together, the improvement comprising:

the conductive element being flexible in embodiment and consists in a further, third spiral wound wire, secured by one end to the spindle and having a length such as to extend from the spindle and terminate near the stimulation electrode anchored to the ventricular wall of the cardiac muscle.

2. An improvement as in claim 1, wherein the sleeve is embodied in two distinct parts comprising a rigid first part affording a longitudinal through socket in which the spindle is rotatably accommodated, and a flexible and tubular second part attached by one end to a corresponding end of the first part and extending a full length of the second spiral wound wire.

3. An improvement as in claim 2, wherein the second part of the sleeve consists in a fourth spiral wound wire secured to the corresponding end of the first part, of which the longitudinal through socket is enlarged for receiving the end of the second spiral wound wire being secured to the spindle, and the fourth spiral wound wire is associated rigidly with the second spiral wound wire at least where the respective free ends coincide.

* * * * *